(12) United States Patent
Paseman et al.

(10) Patent No.: US 8,594,758 B2
(45) Date of Patent: *Nov. 26, 2013

(54) TRANSMISSION FLUOROMETER

(76) Inventors: Sabrina K. Paseman, Saratoga, CA (US); William G. Paseman, Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/547,906

(22) Filed: Jul. 12, 2012

(65) Prior Publication Data

US 2012/0277555 A1    Nov. 1, 2012

Related U.S. Application Data

(63) Continuation of application No. 12/483,967, filed on Jun. 12, 2009, now Pat. No. 8,306,594.

(60) Provisional application No. 61/061,114, filed on Jun. 13, 2008.

(51) Int. Cl.
*A61B 5/1455*    (2006.01)

(52) U.S. Cl.
USPC .......................................................... 600/322

(58) Field of Classification Search
USPC .......................................................... 600/322
See application file for complete search history.

(56) References Cited

U.S. PATENT DOCUMENTS

| | | |
|---|---|---|
| 4,178,917 A | 12/1979 | Shapiro |
| 5,785,658 A | 7/1998 | Benaron et al. |
| 5,933,232 A | 8/1999 | Atzler et al. |
| 6,013,034 A | 1/2000 | Fernandes Da Cunha Vaz et al. |
| 6,252,657 B1 | 6/2001 | Bohnenkamp |
| 6,898,451 B2 | 5/2005 | Wuori |
| 6,985,224 B2 | 1/2006 | Hart |
| 8,306,594 B2 * | 11/2012 | Paseman et al. ............... 600/322 |
| 2005/0177046 A1 * | 8/2005 | Mills ............................... 600/481 |
| 2008/0221415 A1 | 9/2008 | Sweeney |
| 2009/0247845 A1 | 10/2009 | Pav |
| 2009/0312616 A1 | 12/2009 | Paseman |
| 2010/0081144 A1 | 4/2010 | Holmes |

OTHER PUBLICATIONS

"The 1977 Hematofluorometer, schematic diagram," 1977, p. 1.
Beer-Lambert law, Jun. 30, 2009, pp. 1-6, Publisher: Wikipedia.
Paseman, Sabrina, "2008 California State Science Fair," May 6, 2008, p. 1.
"Fluorescence," May 15, 2009, pp. 1-7, Publisher: Wikipedia.
Yuan Yan, Hong Li and M.L. Myrick, "Fluorescense Fingerprint of Waters: Excitation-Emmission Matrix Spectroscopy as a Tracking Tool," 2000, pp. 1539-1542, vol. 54, No. 10, Publisher: Applied Spectroscopy.
"Photomultiplier," May 15, 2009, pp. 1-6, Publisher: Wikipedia.
Paseman, Sabrina, "2008 Project Summary, Project No. S0499," Apr. 2, 2008, p. 1.

(Continued)

*Primary Examiner* — W B Perkey
(74) *Attorney, Agent, or Firm* — Parsons Behle & Latimer

(57) ABSTRACT

This disclosure relates generally to a system and method for noninvasive, non-destructive fluorescent measurement. More specifically, the disclosure provides a non-invasive metrology system and method to monitor levels of fluorescent chemicals in the blood. A major application for the invention is field-based non-invasive blood testing for micro-nutrient deficiency and diseases resulting from it, such as Iron deficient anemia. The invention may help reduce or eliminate the need for blood drawing, sending the sample to a blood lab and having to wait for a result.

29 Claims, 7 Drawing Sheets

(56) References Cited

OTHER PUBLICATIONS

Paseman, Sabrina, "2008 Synopsys Science Competition," Mar. 11, 2008, p. 4.

"Zinc protoporphyrin," May 15, 2009, pp. 1-2, Publisher: Wikipedia.

United States Patent and Trademark Office, Office Action dated Apr. 30, 2012 from U.S. Appl. No. 12/483,967.

* cited by examiner

TRANSMISSION FLUOROMETER

CROSS REFERENCE TO RELATED APPLICATIONS

This application is a continuation of U.S. patent application Ser. No. 12/483,967 filed Jun. 12, 2009, and entitled "Transmission Fluorometer" which claims benefit from U.S. Provisional Patent Application No 61/061,114, filed on Jun. 13, 2008, the disclosure of which are hereby incorporated by reference in their entirety.

FIELD OF THE INVENTION

This disclosure relates generally to a system and method for performing non-invasive and non-destructive transmissive mode and/or fluorescent measurements of chemical analytes in samples that exhibit detectable transparency to both excitation light transmitted through the sample and light fluoresced by the analytes transmitted through the sample. More specifically, a system and method are disclosed to monitor levels of fluorescent chemicals in blood. For such medical applications, the system is safe, easy and sanitary to use compared to existing methods, more convenient than invasive tests, and provides immediate feedback. A major application of the system is field-based non-invasive blood testing of micro-nutrient deficiency and diseases resulting from it, such as iron deficient anemia. The system can potentially be used to initially screen patients for problems, such as micronutrient deficiencies or disease, and may help reduce or eliminate the need for blood drawing, sending the sample to a blood lab and having to wait for a result.

BACKGROUND

Generally, legacy fluorometry systems employ either "right angle" or "front face" optics. Right angle optics is where the detector is placed at right angles to the excitation source. This serves to minimize interference from the excitation source. However, these systems are subject to "inner filtering" problems where the light fluoresced by the sample is filtered out by the sample under test. Front facing optics is where the detector is placed at an angle between either 30-40 degrees or 50-60 degrees to the excitation source. Front facing optics overcomes inner filtering but is unable to relate fluorescent intensity to analyte concentration over a very broad range for analytes having a high extinction coefficient. These problems have limited the application of fluorometry techniques in the area of noninvasive analysis, particularly blood and tissue analysis.

Significant advances in modern technology have failed so far to provide any relief for such problems.

Many of these technologies are disclosed in a broad spectrum of patents and patent applications, including:

U.S. Pat. No. 6,252,657 to Bohnenkamp discloses a reflection fluorometer using light guides to test samples placed in a capillary tube. However this approach is not suitable for non-invasive measurement.

U.S. Pat. No. 5,785,658 to Benaron discloses a tool for nondestructive interrogation of the tissue including a light source emitter and detector which may be mounted directly on a surgical tool in a tissue contacting surface for interrogation or mounted remotely and guided to the surgical field with fiber optic cables. This device is also invasive.

U.S. Pat. No. 5,933,232 to Atzler discloses a measurement station for microtitration plates. The system applies fluorometry to solutions in curvettes, which are not compatible with non-invasive use.

U.S. Pat. No. 6,013,034 to Da Cunha Vaz discloses an Ocular Fluorometer for use in taking non-invasive reflective fluorometric readings of the human eye.

U.S. Pat. No. 4,178,917 to Shapiro discloses a method and system for the non-invasive detection of zinc protoporphyrin (ZPP) in erythrocytes wherein a light source is applied to the skin of the patient. However, the approach uses front facing optics so it is subject to the inherent limitations of front facing optics discussed above.

In summary, the prior art provides a broad range of alternatives to invasive fluorescent spectroscopy. The prior art also provides some solutions to non-invasive spectroscopy using either front facing or reflective optics. However these non-invasive solutions are subject to problems of inner filtering and/or inability to correlate fluorescent intensity to analyte concentration. As a result, existing solutions are inapplicable to a whole host of new applications (such as blood analyte measurement) which demand non-invasive testing, accuracy, broad diagnostic capability and convenient usage.

SUMMARY

The present disclosure addresses the aforementioned problems by providing a novel transmission fluorometry system that can take advantage of the transparency presented by the target material to the exciting and fluorescing wavelengths to measure the relative concentration of analytes. One or more of the following aspects may be realized by the systems and/or methods taught herein:

One aspect of the disclosure relates to non-destructive, non-invasive, fluorescent measurement of samples in the transmission mode. Examples include paper, glass, plastic and in-vivo living tissue such as plant and animal matter.

Another aspect of the disclosure relates to non-invasive blood measurement. Noninvasive Transmission Fluorometry provides a portable, quick, accurate, safe and sanitary system for in vivo, non-invasive detection of several blood ailments such as Iron Deficient anemia.

Another aspect of the disclosure relates to non-invasively detecting multiple blood components using only one excitation wavelength. For example, 365 nm can be used to simultaneously and non-invasively detect Zinc Protoporphyrin, Protoporphyrin IX and Fluorescent Heme Degradation Product, 395 nm can be used to non-invasively detect Zinc Protoporphyrin and Protoporphyrin IX.

Another aspect of the disclosure relates to non-invasively detecting multiple blood components using multiple excitation wavelengths. For example, a sensor head containing both a 425 nm LED and a 346 nm LED can be used to non-invasively detect Zinc Protoporphyrin and Retinol (Vitamin A) simultaneously.

Another aspect of the disclosure relates to normalizing the spectral measurements by dividing each intensity reading in the transmitted spectrum by the height of the excitation wavelength intensity, Normalization allows different readings taken independently to be compared.

One aspect of the disclosure relates to field usage. Most fluorometry systems cannot be used in the field because they are bulky and/or invasive. The present system can potentially be smaller than some fluorometry systems since it may employ relatively small components. As such the instrument can be taken to the subject and does not necessarily require the subject to be brought to the instrument as is the case with existing fluorometers. In addition, the system sensors can be used in vivo on live subjects, as opposed to invasive systems which generally require a sample of the subject to be inserted in a curvette.

Another aspect of the disclosure relates to the measurement point on the subject. Even at high power, UV does not penetrate far enough to go through traditional measurement points such as an earlobe or a finger. In addition, the usage of UV precludes testing the palebral conjunctiva due to safety considerations. However, the method described in the present disclosure, namely shining an excitation wavelength through a section of loose skin on the subject (such as webbing between finger and thumb), can produce the desired results. In an embodiment, a clamping system can be employed whereby the thickness of the sample can be intentionally reduced to a suitable thickness, such as, for example, a thickness ranging from about $\frac{1}{8}^{th}$ inch or less, such as approximately $\frac{1}{16}^{th}$ inch. In an embodiment, the clamping system may also result in the sample being blanched, thereby reducing the concentration of analytes.

Another aspect of the disclosure relates to sensor size. Most Sensor/Fluorometer systems cannot be used in the field, due to their bulkiness. In addition to permitting portable "in vivo" measurement, the sensor in the preferred embodiment is narrow enough to pinch the skin between thumb and forefinger in a child's hand.

Another aspect of the disclosure relates to measuring and reporting a broad spectrum of analyte ratios simultaneously. Some analyte ratios (e.g. ratio of oxygenated hemoglobin to total hemoglobin) are most easily measured using absorption spectroscopy. The system of the present disclosure can perform "mixed mode" measurements involving both fluorometry and absorption spectroscopy on the subject simultaneously, via reflectance if necessary, in order to report a broader range of analyte ratios.

Further aspects of this disclosure will become apparent in the Detailed Description and by reference to the attached drawings.

DETAILED DESCRIPTION

In the following description, reference is made to the accompanying drawings, which form a part hereof, and which show, by way of illustration, specific embodiments or processes in which the teachings of the present disclosure may be practiced. Where possible, the same reference numbers are used throughout the drawings to refer to the same or like components. In some instances, numerous specific details are set forth in order to provide a thorough understanding of the present disclosure. The teachings of the present disclosure, however, may be practiced without the specific details or with certain alternative equivalent devices and methods to those described herein. In other instances, well-known methods and devices have not been described in detail so as not to unnecessarily Obscure aspects of the present disclosure.

I. System Overview and Components

Figure 1:
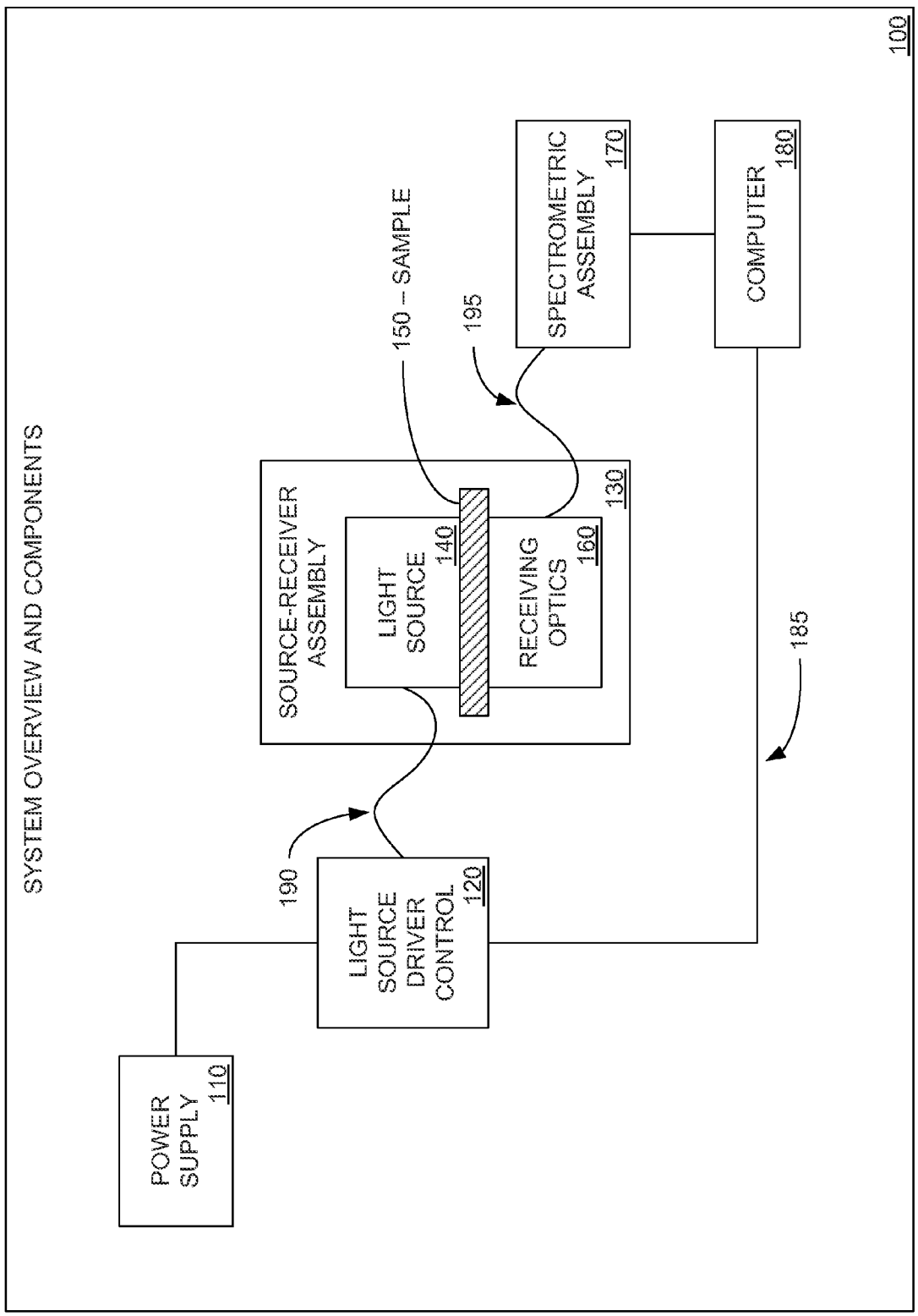
FIG. 1 illustrates a system overview and components, according to an embodiment of the present disclosure.

FIG. 1 illustrates the system overview and components of an embodiment of the transmission fluorometry system 100 of the present disclosure. In the embodiment shown in FIG. 1, the system 100 comprises a power supply 110 coupled to a light source driver control 120. The light source driver control 120 is coupled via any suitable electrical connection 190 to a source-receiver assembly 130, which comprises a light source 140 and receiving optics 160. A spectrometric assembly 170 can be coupled to the receiving optics 160 via any suitable optical link 195 for providing a spectral data output of the light transmitted through and/or emitted from the sample 150. The spectral data 170 can be fed into a computer 180 for analysis.

In operation, the power supply 110 powers light source driver control 120. Any suitable power supply can be employed. Examples of suitable power supplies that can be employed include battery power, USB cable, and/or electrical outlet power.

The type of power supply 110 may depend on the intended use of the system 100 and can potentially enhance the convenience of employing the system 100, For example, if the system 100 is used only to take absorption measurements versus fluorescent measurements, it can run on battery power for relatively long periods of time (e.g. several days of continuous operation, depending on the battery technology employed). The system 100 can also be powered from the USB port of a personal computer 180. This is a convenient arrangement when the goal is, for example, to continuously upload readings from the spectrometric assembly 170 over the same USB cable, because it means that the system 100 does not require any extra external power connection. It is also convenient when the system 100 needs to be taken out in the field, because the user can then view the system 100 as a peripheral (much the same way as a USB memory stick is viewed as a peripheral) that simply attaches to the computer 180. The power supply 110 can run off of wall current if, for example, the goal is to provide continuous monitoring over a long period of time.

The light source driver control 120 drives one or more excitation light sources 140, mounted on the source-receiver assembly 130. Any suitable light source driver can be employed. For example, the light source driver control 120 can be a manual system of switches and potentiometers or an automatic electronic system controlled from the computer 180 in a closed loop configuration.

In an embodiment, the computer 180 provides continuous monitoring of the sample 150 and adjusts the light source 140 brightness via the automatic electronic system based on how much light is being transmitted through the sample 150, as well as how much fluorescence is being detected by the receiving optics 160. In this case, a control loop 185 for controlling the light source can be driven automatically without any manual intervention whatsoever. The source-receiver assembly 130 contains a light source 140 that irradiates the Sample 150, which in turn transmits both light from the light source 140 and fluoresced light from analytes in the sample 150. This light is detected by the receiving optics 160 which provides input to a spectrometric assembly 170.

In an embodiment, the source-receiver assembly can contain one or more LED light sources 140. Light from the light source 140 can excite several analytes in the sample 150 and passes a single spectrum via the receiving optics 160 to the spectrometric assembly 170. The receiving optics 160 may comprise, for example, a collimating lens that connects to the spectrometric assembly 170 via a fiber optic cable 195.

In an embodiment, light source 140 can be configured as a set of LEDs clustered together on a single clip arm or a single chip substrate. The LEDs can be turned on and off in sequence, exciting a series of spectrums in the sample 150 that pass through the receiving optics 160 and are transmitted to the spectrometric assembly 170. In this manner, it is possible to detect multiple components using multiple excitation wavelengths. For example, a sensor head containing both a 425 nm LED and a 346 nm LED can be used to non-invasively detect Zinc Protoporphyrin and Retinol (Vitamin A) simultaneously.

Figure 4:
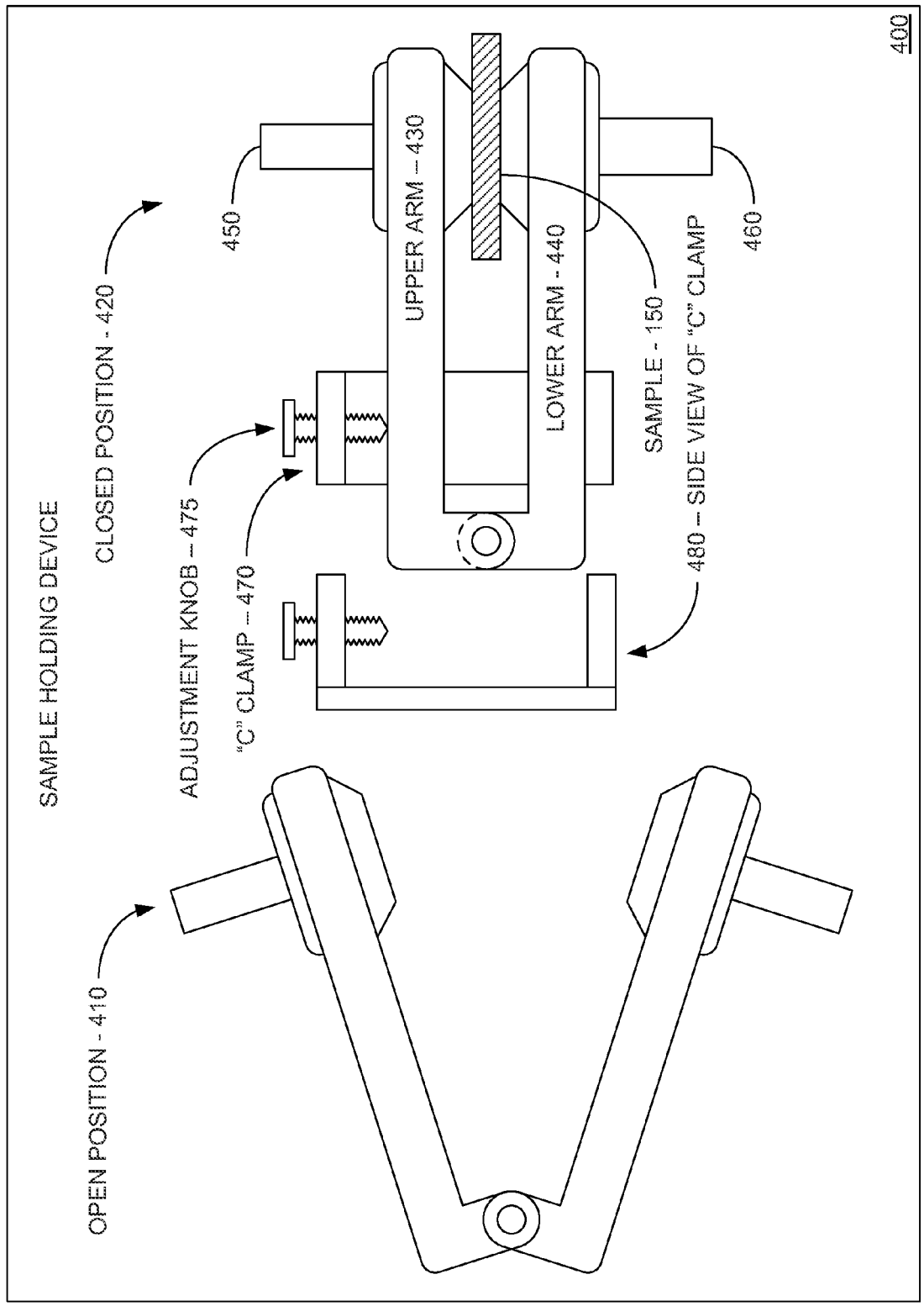
FIG. 4 illustrates a sample holding device, according to an embodiment of the present disclosure.
Figure 5:
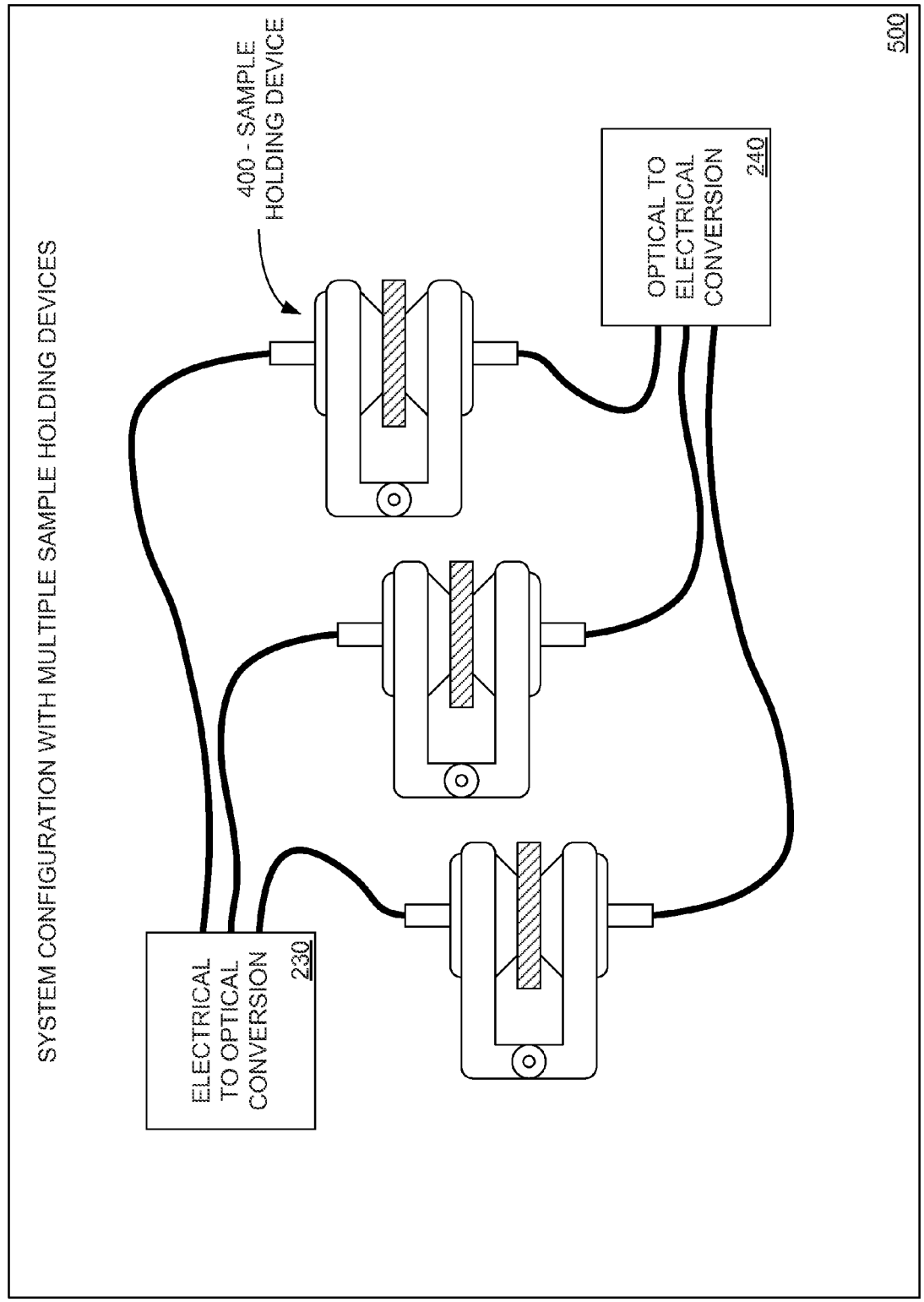
FIG. 5 illustrates a configuration with multiple sample holding devices, according to an embodiment of the present disclosure

In one embodiment, the source-receiver assembly 130 can be configured as a sample holding device, illustrated in FIG. 4, that pinches the sample between the light source 140 and the receiving optics 160. The decoding and analysis of the set of spectrums can then be done by the computer 180. The source-receiver assembly can include, for example, a sample holding device 400 having an upper arm 430 and a lower arm 440. FIG. 4 illustrates a sample holding device 400 in an open position 410 and a closed position 420. The source-receiver assembly 130 may include a set of sample holding devices 400, as shown in FIG. 5, each with a single or multiple LED light source 140, as described previously. This configuration can be used if, for example, the tester wants to take simultaneous measurements of different parts of the subject 150 at the same time. If the tester wants a narrowed spectrum light, the source-receiver assembly 130 can employ laser diodes as light sources 140 in place of the LEDs. If the tester wants more exact wavelength control, the source-receiver assembly 130 can employ a traditional monochromator as a Light Source 140.

The spectrometric assembly 170 can be a single spectrometer, such as an OceanOptics USB2000, which connects to the computer 180 via, for example, a USB port. An alternate embodiment is a spectrometric assembly 170 with a set of photodiode/filter pairs where each pair is tuned to either the excitation wavelength or fluorescent emission peaks of analytes of interest. For high resolution applications, a high sensitivity version of the spectrometric assembly 170 can employ a single photomultiplier tube or charge coupled device (CCD) array, and the filters can be successively passed over the active area of the receiving optics in order make the device sensitive to the wavelengths of interest. In light of the disclosure herein, providing any of the above mentioned spectrometric assemblies is well within the ordinary skill of the art.

The spectrometric assembly 170 is linked to a computer 180. The computer 180 can be a "personal computer" running spectrographic analysis algorithms. However, in the event the tester wants to provide continuous monitoring in a small form factor, the computer 180 can be a micro-controller, such as, for example, a member of the Texas Instruments MSP430FG43x: mixed signal microcontroller family. In this case, the computer 180 can, for example, monitor the input spectrum from the spectrometric assembly 170, control the light source 140 through the light source driver control 120 via the control loop 185, analyze the spectrum and convert the results to human readable form.

Figure 2:
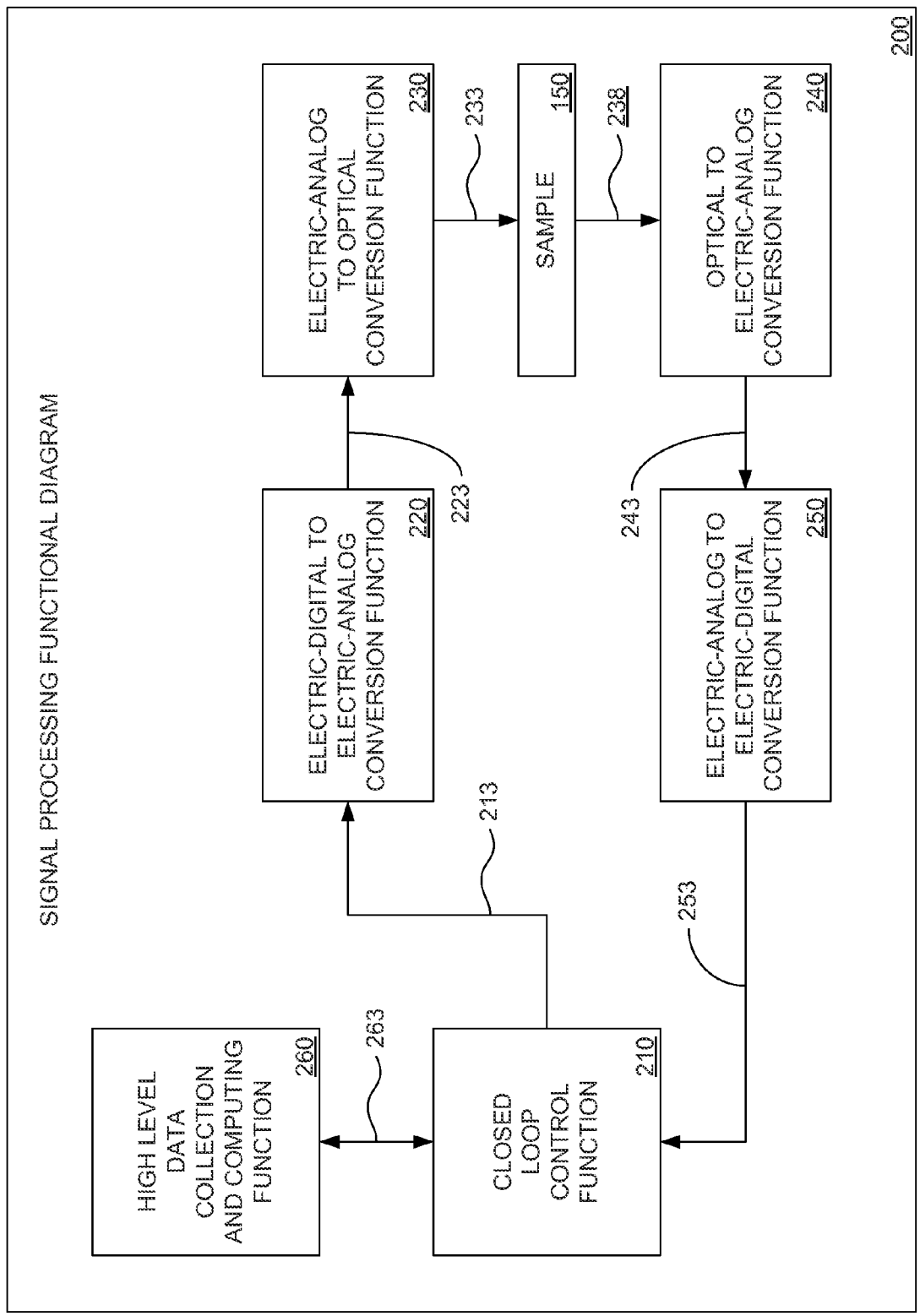
FIG. 2 illustrates a signal processing functional diagram, according to an embodiment of the present disclosure.

FIG. 2 illustrates a signal processing functional diagram 200, according to an embodiment of the present disclosure. A closed-loop control function 210 passes an electric-digital control representation 213 to an electric-digital to electric-analog conversion function 220. The electric-digital to electric-analog conversion function 220 passes an electric-analog representation 223 to an electric-analog to optical conversion function 230. The electric-analog to optical conversion function 230 generates an incident optical signal 233 which is directed to a first surface of the sample 150. An optical signal 238 emerging from a second surface of the sample 150 is received by an optical to electric-analog conversion function 240. The optical to electric-analog conversion function 240 passes an electric-analog representation 243 to an electric-analog to electric-digital conversion function 250. The electric-analog to electric-digital conversion function 250 passes an electric-digital representation 253 back to the closed-loop control function 210. A high level data collection and computing function 260 communicates with the closed-loop control function 210 through an interface function 263.

In operation, an embodiment of the closed loop control function 210 can be configured to provide control instructions for the electric-digital to electric-analog conversion function 220, the electric-analog to optical conversion function 230, data gathering for the optical to electric-analog conversion function 240 and the electric-analog to electric-digital conversion function 250.

The closed loop control functions can be either manual or automatic. Any suitable closed-loop control function can be employed. A manual control function uses an operator to read feedback parameters such as noise and received light intensity at particular wavelengths and computed functions thereof (e.g. $SpO_2$ level) and to manually adjust the incident light intensity, duration and physical and temporal point of measurement in order to get a strong signal that does not swamp the receiving optics. An automatic control function is performed automatically in real-time and can be implemented using micro controllers such as, for example, Atmel's AVR or Texas Instrument's MSP430. In one embodiment, the closed loop control function 210 can be a pulse oximeter, which can take, for example, red and infrared light absorption readings every 1 ms using a standard pulse oximetry probe. These readings can be smoothed by the closed loop control function 210 and transmitted to the high level data collection and computing function 260 in order for the system to monitor and record sample data. The closed loop control function 210 may also receive commands from the high level data collection and computing function 260, allowing it, for example, to take additional readings with other wavelengths, at desired points in time and for desired durations.

In an embodiment, the electric-digital to electric-analog conversion functions 220 can be used to convert a digital control representation 213 to an analog representation 223. In one embodiment, the digital control representation 213 may be used to select a desired light source and an associated intensity with which to illuminate the sample. In this case, the electric-digital to electric-analog conversion function 220 may convert the digital control representation 213 to a set of analog signals at various voltage or current levels (including zero) to drive the electric-analog to optical conversion function 230. The electric-digital to electric-analog conversion function 220 can be performed with a digital to analog converter (DAC). The DAC may be a standalone unit, or integrated with the closed loop control function 210 as in the case of, for example, the MSP430.

In an embodiment, the electric-analog to optical conversion function 230 can be used to convert the analog electrical representation 223 to the light signal that illuminates the sample. This function can be implemented for example as one or more LEDs or laser diodes mounted on a semiconductor chip, as a bundle of fibers connecting to an array of LEDs or laser diodes mounted on a board, or as a single light source with a switchable set of filters. The electric-analog to optical conversion function 230 may be for example a standalone unit, or integrated with the optical to electric-analog conversion function 240 as in the case of, for example, a Nellcor Pulse Oximeter probe.

In an embodiment, the optical to electric-analog conversion function 240 is used to convert the light signal that is received from the sample 150 to an electric-analog representation 243. The optical to electric-analog conversion function 240 can be, for example, a photodiode as used in a pulse oximeter; a diffraction grating and CCD array as used in a spectrometer, such as the OceanOptics USB 2000; or a Photomultiplier tube, such as used in a Fluorimeter. The optical to electric-analog conversion function 240 may be a standalone unit, or integrated with the electric-analog to electric-digital conversion function 250, as used, for example, in an OceanOptics Spectrometer.

In an embodiment, the electric-analog to electric-digital conversion function 250 can be used to convert an analog representation 243 to a digital control representation 253. In an embodiment, this conversion can be an analog to digital converter (ADC). The electric-analog to electric-digital conversion function 250 may be, for example, a standalone unit, or integrated with the closed loop control function 210 as in, for example, the Texas Instrument's MSP430.

In an embodiment, the high level data collection and computing function 260 can communicate with the closed-loop control function 210 to transmit instructions and receive and store data. The high level data collection and computing function 260 can be any suitable computing device such as, for example, a personal computer, a handheld computer or a laptop computer.

The functions closed-loop control 210, electric-digital to electric-analog conversion 220, electric-analog to electric-digital conversion 250, and high level data collection and computing 260, could potentially be performed manually by an operator, but any such embodiments would be of little value compared to automated functions offered by modern technology.

Figure 3:
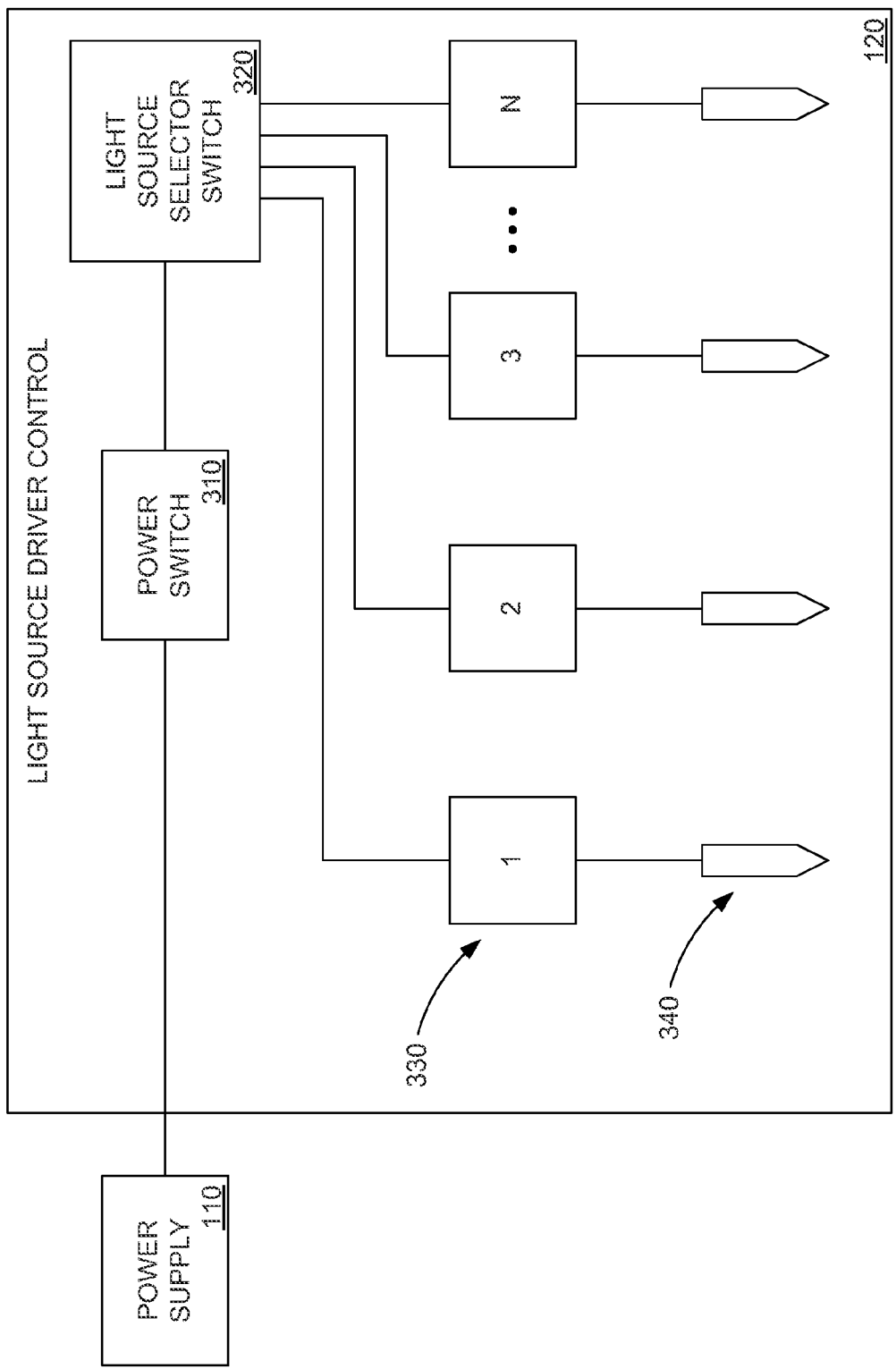
FIG. 3 shows a light source driver control, according to an embodiment of the present disclosure.

FIG. 3 illustrates an embodiment of the light source driver control 120. Current from the power supply 110 flows through power switch 310, which controls when power is applied to the source-receiver assembly 130 to excite the sample and generate a fluorescent output characteristic of the analytes to be measured. The light source selector switch 320 provides flexibility to select any configuration of light sources 140 that may be appropriate to optimize a particular application. The intensity of each light source 140 can be independently controlled by a light source intensity controller 330, either manually or automatically. In one embodiment, the light source intensity can be automatically set by a control algorithm running on the computer 180 to a desirable level that optimizes the dynamic range and signal to noise ratios of the detected excitation and/or the analyte spectral signals. In an embodiment, the intensity controllers 330 can be connected to light source connectors 340, which can provide for a desired connectability to the light source 140 (e.g., LEDs).

FIG. 4 illustrates an embodiment of the source-receiver assembly 130 in the form of a sample holding device 400. The sample holding device 400 is illustrated in both an open position 410 and a closed position 420. The sample 150 to be measured can be held between one or more light sources 140 mounted on the upper arm 430 of the sample holding device 400 and the receiving optics 160 mounted on the lower arm 440 of the sample holding device 400. Employing appropriate sample thicknesses can allow for the desired transmission of light (e.g., light from the light source 140 and/or fluoresced light) through the sample. For example, sample thicknesses can be consistent with a desired resolution of quantitative measurements of intensity of both excitation light transmitted through the sample and the fluoresced light emitted by blood analytes upon excitation by the light source. Examples of samples for which the clip mechanism is desirable include: a thin film, the webbing between a subject's index finger and thumb, the subjects ear, the subject's nose, the subject's cheek, a section of loose skin on a subject's wrist or elbow joint or any other part of the subjects body where a desired sample thickness can be identified. When applying the sample holding device 400 to a subject for blood testing, the pressure blanches the skin, resulting in a dilution effect of the blood in the sample, which minimizes inner filtering. A light source connection device 450 can provide a connection to light source driver control 120. A receiving optics connection device 460 can provide a connection to the spectrometric assembly 170.

FIG. 4 also shows a "C" clamp 470 to illustrate a mechanism to control the sample thickness by compressing the gap between the upper and lower arm of the sample holding device 400. Also shown are an adjustment knob 475 and a side view of the "C" clamp 480. In other embodiments, the mechanism to control the sample thickness can use a variety of modern technologies. Examples of such technologies include: a piezoelectric crystal based system attached to the arm, a hydraulic based system consisting of a pressurized liquid filled cylinder and a pneumatic based system with a pressurized air filled bag. An additional advantage of these modern technologies is the capability to provide a way to control sample thickness without completely blanching the tissue.

The mechanism to control the sample thickness may improve the results obtained using the system of the present application for cases where the wavelengths of interest are heavily attenuated by the sample. For example, measurements of zinc protoporphyrin (ZPP) at wavelengths in the ranges of 346 to 370 nm, 390 to 400 nm and 420 to 430 nm in a sample of in vivo skin, can be more reliably obtained where the skin can be pinched to a suitable thickness.

In accordance with the Beer-Lambert law, the attenuation of light within the sample increases exponentially with the sample thickness and analyte concentration. The use of a sample holding device configured to provide controlled reductions of the sample thickness can have two beneficial effects. It can cause a reduction of the sample thickness while at the same time it may also reduce the concentration of analytes by a blanching process. While not intending to be limited by theory, it is believed that a significant increase in detected intensity can be achieved due to one or more of these benefits. For example, a ½" thick sample of hemoglobin irradiated with 10 lumens of light at 940 nm will produce an output intensity of approximately 0.00263 lumens. For comparison, a comparable output intensity can be obtained with a 1/16" inch thick sample of hemoglobin that has been diluted by a factor of 32 by blanching and is irradiated with the same 10 lumens of light at 426 nm. These considerations illustrate a potential advantage of the aforementioned sample holding device, which is that it can allow transmission fluorimetry to determine analyte concentration ratios via light absorption and fluorescence at wavelengths outside of the "medical spectral window" of 600-1100 nm. Thus, the systems of the present application can employ wavelengths of less than 600 nm, such as for example, wavelengths in the ranges of 346 to 370 nm, 390 to 400 nm and 420 to 430 nm. Wavelengths outside of these example ranges can also be employed, including wavelengths within the medical spectral window.

Although FIG. 4 shows a very simple mechanism to control the sample thickness, other implementations can use more desirable systems to achieve the objectives outlined herein, such as reducing sample thickness and/or blanching the sample. In light of the disclosure herein, providing any of the above mentioned thickness control systems is well within the ordinary skill of the art.

Figure 6:
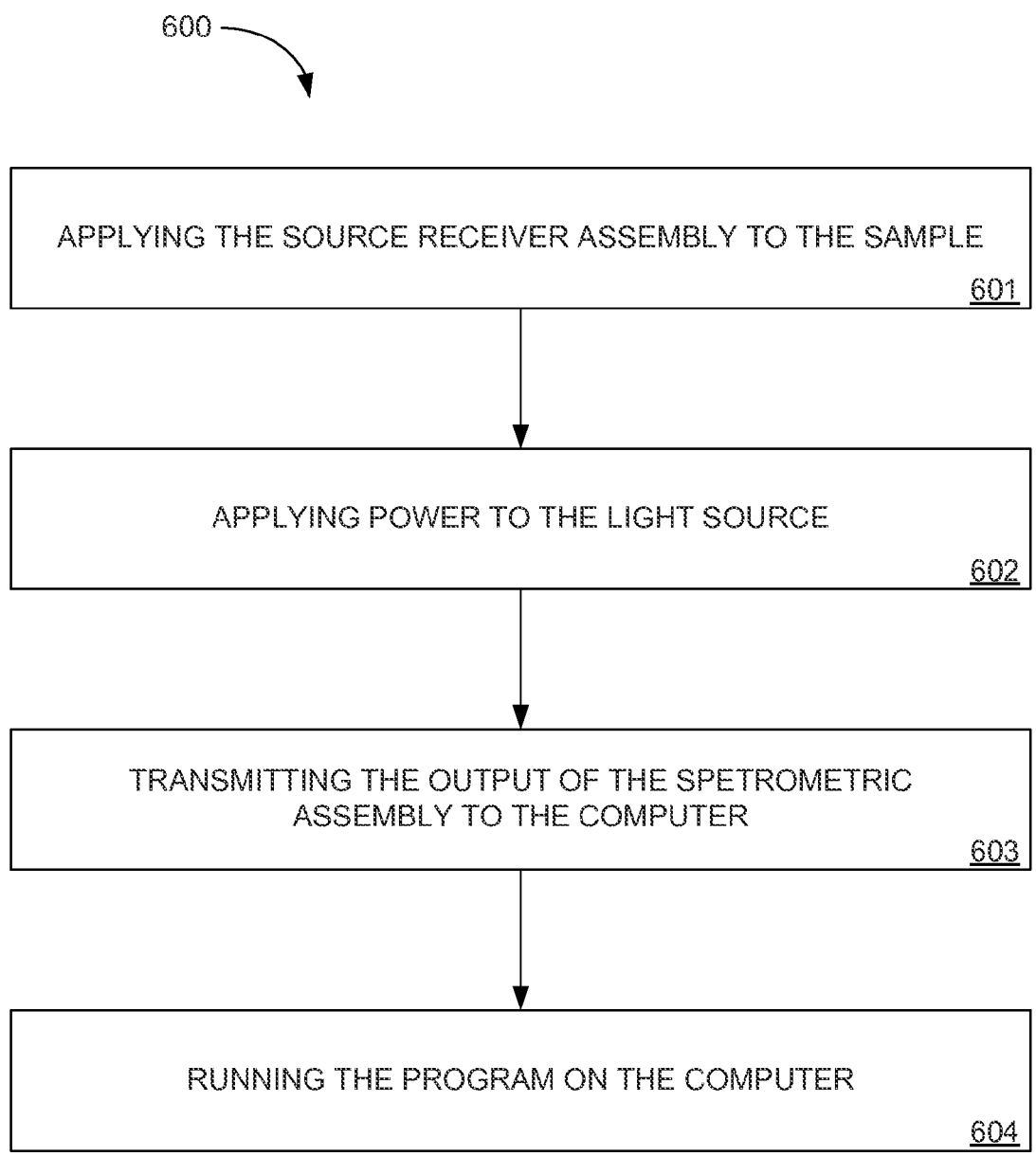
FIG. 6 is a flowchart illustrating a method performed by the fluorescent measurement system.

FIG. 6 is a flowchart illustrating a preferred method 600 by which the transmission fluorometry system 100 can collect normalized fluorometry data from a sample. At 601, the source-receiver assembly 130 is applied to the sample 150. At 602, power is applied to the light source 140. At 603, the output from the spectrometric assembly 170 is transmitted to the computer 180. At 604, a computer program is run. The computer program can compute, for example, the relative concentrations of two or more analytes present in the sample 150 based upon spectral outputs collected by the spectrometric assembly 170.

In an embodiment, analyte ratios can be computed by using "absorption only" techniques such as those used by pulse oximeters. For example pulse oximeters compute heart rate and blood $O_2$ concentration using measurements of the relative absorption of blood and surrounding tissue at two different wavelengths over time.

In another embodiment, these analytes may be computed by using "fluorescence only" techniques, such as algorithms that look at the ratios of emission heights from the same excitation wavelength. The ratios of the heights of multiple emission peaks can be calculated. Exemplary ratios include the ratio of primary to secondary emission peaks of the analyte Zinc Protoporphyrin when excited at 425 nm or the ratio of the primary emission peak of Zinc Protoporphyrin to Protoporphyrin IX when both are excited at 365 nm. In yet another embodiment, a technique employing a ratio of ratios can used, which compares the ratio of one set of excitation and emission peaks to the ratio of another set of excitation and emission peaks. Calculating a ratio of ratios is generally well known in the art.

In yet another embodiment, analytes may be computed by using "mixed absorption and fluorescence" techniques, such as one that would look at the ratios of emission heights to absorption ratios which occur when the same tissue is irradiated by two or more light sources that are placed very near each other. An example is the ratio of Hemoglobin absorption to ZPP fluorescence relative to the ratio of their respective irradiation light intensities. These analytes may also be computed by using "time resolved methods" or "frequency resolved methods". For example, one such method distinguishes between two analytes with similar spectral signatures by measuring their fluorescent lifetimes. Given the present disclosure, one of ordinary skill in the art would be able to employ the systems disclosed herein to detect analytes using absorption only, fluorescence only and mixed absorption and fluorescence techniques.

II. Normalizing Data

Figure 7:
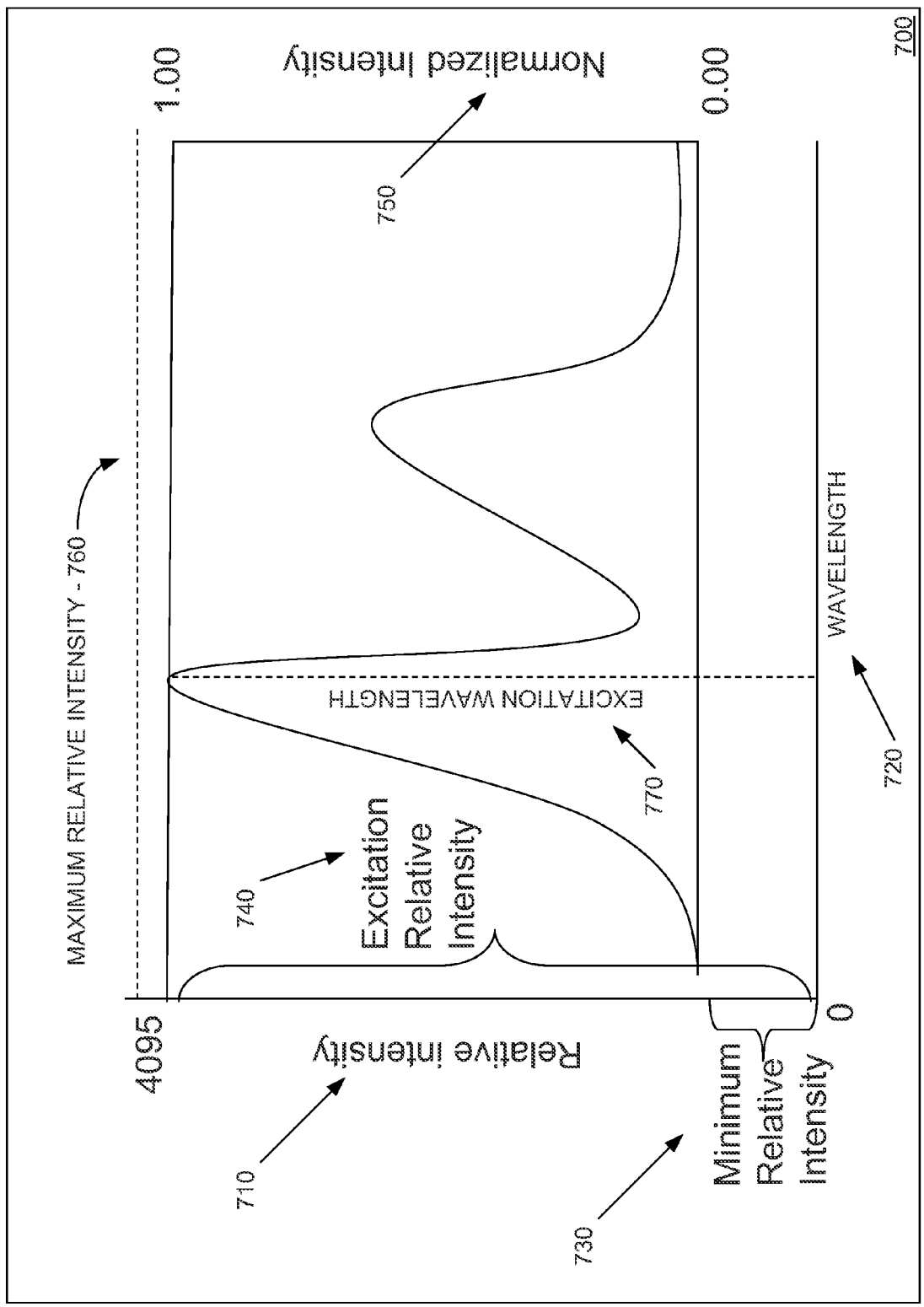
FIG. 7 is a diagram illustrating how to normalize a transmission fluorometer reading.

Fluorometry data taken from the sample can be normalized to allow different readings taken independently to be compared. Any suitable method of normalizing the data can be employed. FIG. 7 illustrates an embodiment of a sample normalization algorithm 600. A spectrometric assembly 170 organizes data in terms of a graph of relative intensity 710 versus wavelength 720. For illustrative purposes, relative intensity 710 can be an integer that ranges from 0 to a maximum relative intensity 760 of 4095, as depicted in FIG. 7. To allow intensity data from different light sources 140 examining the same subject at the same time to be compared to each other, the intensity can be normalized. This is done by first determining the "minimum relative intensity" 730, which is the smallest intensity recorded by the spectrometric assembly 170 for the sample 150. Next, the "excitation relative intensity" 740 is determined by looking up the intensity at the excitation wavelength 770. Finally, a normalized intensity value is calculated at each wavelength by taking the relative intensity reading at that wavelength, subtracting the minimum relative intensity 730, and dividing this difference by the difference between the excitation relative intensity 740 and the minimum relative intensity 730. If done for each wavelength, this algorithm will produce a graph of normalized intensities 750 where the intensity at the excitation wavelength 770 will have a value of "1.00" with all other intensities scaled relative to it.

III. Conclusion

Although this invention has been described in terms of certain preferred embodiments, other embodiments that are apparent to those of ordinary skill in the art, including embodiments that do not provide all of the features and advantages set forth herein, are also within the scope of this invention. Therefore, the scope of the present invention is defined only by reference to the appended claims and equivalents thereof.

What is claimed is:

1. A non-invasive measurement system for determining ratios of concentrations of at least two analytes in a sample area, the system comprising:
    a light source configured to provide an output spectrum which excites the at least two analytes at each of a plurality of discrete locations within a sample area;
    an image sensing assembly capable of sensing the intensity and wavelength of fluoresced light emitted by the at least two analytes upon excitation by the light source at each of the plurality of discrete locations within the sample area; and
    a computer system linked to the image sensing assembly, the computer system comprising computer readable code for computing and providing as output the ratio of the concentration of one analyte relative to the concentration of at least another analyte for each of the plurality of discrete locations within the sample area.

2. The system of claim 1, further comprising receiving optics positioned relative to the light source so as to receive the fluoresced light, the receiving optics being coupled to the image sensing assembly.

3. The system of claim 1, wherein the output comprises a graphical representation of the sample area.

4. The system of claim 1, wherein the image sensing assembly comprises a charge coupled device array.

5. The system of claim 1, further comprising at least two filters, each filter corresponding to an emission wavelength of one of the at least two analytes.

6. The system of claim 5, wherein the at least two filters are arranged so that the filters may be successively placed between the light source and the image sensing assembly.

7. The system of claim 1, wherein the light source comprises an LED, laser diode or monochromator.

8. The system of claim 1, wherein the light source emits a wavelength chosen from the ranges of about 346 to about 370 nm, about 390 to about 400 nm and about 420 to about 430 nm.

9. The system of claim 1, wherein the light sources emits wavelengths that excite micro-nutrients.

10. The system of claim 2, further comprising a source-receiver assembly configured to maintain optical alignment between the light source and the receiving optics, whereby the sample is pinched between the light source and the receiving optics.

11. The system of claim 2, further comprising a sample holding device configured to hold the sample in a source-receiver assembly between the light source and the receiving optics.

12. The system of claim 11, wherein the sample holding device is configured to pinch a sample to a thickness consistent with measurements at wavelengths chosen from the ranges of about 346 to about 370 nm, about 390 to about 400 nm and about 420 to about 430 nm.

13. The system of claim 10, wherein the source-receiver assembly is configured to receive feedback from the computer to support automatic control of the light source.

14. The system of claim 1, wherein the computer readable code comprises instructions for employing absorption-based analyte identification algorithms to detect non-fluorescing analytes.

15. The system of claim 1, wherein the computer readable code comprises instructions for employing analyte identification algorithm to detect fluorescing analytes.

16. The system of claim 1, wherein the light source comprises multiple LEDs, each LED emitting light over a different range of wavelengths.

17. The system of claim 2, wherein the receiving optics are positioned at an angle of about 180° relative to the light source.

18. The system of claim 2, wherein the receiving optics are positioned at an angle of greater than 90° relative to the light source.

19. The system of claim 1, wherein the computer readable code comprises instructions for computing the ratios of heights of multiple emission peaks to determine the ratio of the concentration of one analyte to the concentration of another analyte.

20. The system of claim 1, wherein the computer readable code comprises instructions for computing the ratio of one set of excitation and emission peaks to the ratio of another set of excitation and emission peaks to determine the ratio of the concentration of one analyte to the concentration of another analyte.

21. The system of claim 1, wherein the image sensing assembly is further capable of sensing an unabsorbed portion of the output spectrum provided by the light source.

22. A method for employing the non-invasive system of claim 1, the method comprising:
    pinching the sample area into a space between the light source and the image sensing assembly;
    applying power to the light source, wherein the power level of the light source is set to a level that causes the image sensing assembly to produce an output;
    transmitting the output of the image sensing assembly to the computer system; and
    running the at least one program in the computer system.

23. The method of claim 22 wherein the sample area comprises in vivo skin.

24. The method of claim 23 wherein the sample area is the webbing between a patient's thumb and forefinger.

25. A method for employing the non-invasive system of claim 10, the method comprising:
    applying the source-receiver assembly to the sample area whereby the sample area is pinched between the light source and the receiving optics;
    applying power to the light source, wherein the power level of the light source is set to a level that causes the image sensing assembly to produce an output;
    transmitting the output of the image sensing assembly to the computer system; and
    running the at least one program in the computer system.

26. The method of claim 25 wherein the sample area comprises in vivo skin.

27. The method of claim 26 wherein the sample area is the webbing between a patient's thumb and forefinger.

28. The method of claim 22 wherein the sample area is on the patient's ear.

29. The method of claim 26 wherein the sample area is on the patient's ear.

* * * * *